(12) United States Patent
Goldstein

(10) Patent No.: US 6,448,571 B1
(45) Date of Patent: Sep. 10, 2002

(54) RADIATION PROTECTION SYSTEM

(76) Inventor: James A. Goldstein, 1645 Hillwood Dr., Bloomfield Hills, MI (US) 48304

(*) Notice: Subject to any disclaimer, the term of this patent is extended or adjusted under 35 U.S.C. 154(b) by 0 days.

(21) Appl. No.: 09/638,772

(22) Filed: Aug. 15, 2000

(51) Int. Cl.[7] ............................. G21F 7/00; G21F 3/02
(52) U.S. Cl. ................................ 250/515.1; 250/516.1; 250/505.1; 378/189; 378/167
(58) Field of Search ..................... 250/515.1, 505.1, 250/516.1, 517.1; 378/189, 167

(56) References Cited

U.S. PATENT DOCUMENTS

| | | |
|---|---|---|
| 1,907,523 A | 5/1933 | Egressi et al. |
| 3,299,270 A | 1/1967 | D'Avella |
| 3,308,297 A | 3/1967 | Mansker |
| 3,904,695 A | 9/1975 | Hendrickx et al. |
| 4,062,518 A | 12/1977 | Stivender et al. |
| 4,074,141 A | 2/1978 | Bryant |
| 4,400,623 A | 8/1983 | Jacobson |
| 4,460,833 A | 7/1984 | Malamud et al. |
| 4,514,640 A | 4/1985 | Bagnell et al. |
| 4,581,538 A * | 4/1986 | Lenhart .................... 250/519.1 |
| 4,638,166 A | 1/1987 | Baudro |
| 4,729,869 A | 3/1988 | Schukei et al. |
| 4,938,233 A * | 7/1990 | Orrison et al. .............. 128/849 |
| 5,006,718 A | 4/1991 | Lenhart |
| 5,090,044 A | 2/1992 | Kobayashi |
| 5,417,225 A * | 5/1995 | Rubenstein et al. ........ 128/849 |
| 5,483,562 A | 1/1996 | Kornfeldt et al. |
| 5,506,882 A | 4/1996 | O'Farrell, Jr. et al. |
| 5,564,438 A | 10/1996 | Merchant |
| 5,586,163 A | 12/1996 | Goldstein |
| 5,842,987 A | 12/1998 | Sahadevan |
| 5,981,964 A * | 11/1999 | McAuley et al. ........ 250/515.1 |
| 5,994,706 A | 11/1999 | Allen et al. |
| 6,105,578 A | 8/2000 | Sommers et al. |
| 6,282,264 B1 * | 8/2001 | Smith et al. ................. 378/189 |

OTHER PUBLICATIONS

Nuclear Associates; Clear–Pb Lead–Plastic Multipurpose Adjustable–Height Mobile Barrier, Apr. 2000, 6 pages, New Jersey, United States of America.

Worldwide Innovations & Technologies, Inc.; Breakthrough Technology In Radiation Protection, 3 pages, Kansas, United States of America.

Randall, Tina M., et al.; Neuro–Oncology Update: Radiation Safety and Nursing Care During Interstitial Brachytherapy, Journal of Neuroscience Nursing, Dec., 1987, vol. 19, No. 6.

Sewchand, Wilfred, et al.; Radiation Control in the Intensive Care Unit for High Intensity Iridium–192 Brain Implants, Neurosurgery, vol. 20, No. 4, p. 584.

Ross, Allan M., et al.; Prevalence of Spinal Disc Disease Among Interventional Cardiologists, The American Journal of Cardiology, 1997, vol. 79, No. 1.

Clark, David A.; Editorial Comment: How Much Is Too Much?, Catheterization and Cardiovascular Interventions, 2000, No. 51, p. 285.

Balter, Stephen; An Overview of Radiation Safety Regulatory Recommendations and Requirements, Catheterization and Cardiovascular Interventions, 1999, No. 47, p. 469–474.

* cited by examiner

*Primary Examiner*—Jack Berman
*Assistant Examiner*—Kalimah Fernandez
(74) *Attorney, Agent, or Firm*—Sonnenschein Nath & Rosenthal; Michael T. Marrah; G. Harley Blosser

(57) ABSTRACT

A radiation protection system around a patient on an x-ray table includes a radiation protection wall with an opening around the x-ray table, a radiation screen over the patient, and a flexible interface joining the cubicle and the x-ray table. The wall shields medical personnel in an operating region from most radiation output by an x-ray emitter. The radiation screen is attached to the x-ray table such that it can be retracted to the foot of the x-ray table and extended over the patient such that it is interposed between the patient and the medical personnel. The interface has flexible joints attached to the wall and a flexible radiation-resistant skirt that joins the wall to the screen and covers the opening in the wall. An access port may be formed in the screen, and a shielding cloak can cover the access port to surround medical instruments that are threaded through the port and inserted into the patient.

19 Claims, 4 Drawing Sheets

RADIATION PROTECTION SYSTEM

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

This invention relates generally to radiation shielding devices and, more particularly, to adjustable radiation shielding devices for medical procedures using x-ray radiation to create internal images of a patient.

2. Description of Related Art

X-rays are used in a wide variety of medical procedures, many of which require medical personnel to be in direct contact with the patient, thereby exposing such personnel to radiation. For this reason, both fixed and mobile lead shields are employed in fluoroscopic procedures to minimize radiation exposure. Such shields typically are constructed of radiation resistant plates suspended on bars that are adjusted to be interposed between the operators and the patient on the x-ray table. Despite the use of these shields, medical personnel are still exposed to radiation. It is therefore imperative that such personnel wear leaded protective clothing (including full lead aprons, thyroid collars and leaded glasses). In addition, the doctors performing these radiologic procedures typically spend many hours per day, several days per week over many years throughout their medical careers in such procedures. This long term, cumulative exposure may cause adverse effects. Furthermore, the wearing of heavy lead aprons may have long term deleterious effects resulting in disabling disorders of the spine in a significant number of operators.

There are prior art patents for protecting and shielding against radiation in x-ray laboratories. The inventions in the prior art describe various shields made of radiation resistant material that are either mobile or attached to the x-ray table and can be adjusted between the operators and the x-ray source. Though there are numerous shapes and designs for these shields, and although they may be constructed of various materials, they do not sufficiently protect against radiation exposure, and medical personnel must still wear heavy and encumbering leaded protective clothing.

When working with a patient on an x-ray table, doctors and other medical personnel can be exposed to primary radiation that emanates directly from the source or can be exposed to secondary radiation that is scattered by an object such as the x-ray detector, the x-ray table, and even the patient. No prior invention has sufficiently reduced the radiation in the operating region of an x-ray laboratory by using a radiation shield on an x-ray table in combination with a radiation containment enclosure and a radiation leak-resistant interface between the enclosure and the table. Furthermore, no previous invention has included such a shield with access ports or has included such an enclosure with access panels, equipment platforms, and interfaces for table controls.

BRIEF SUMMARY OF THE INVENTION

It is in view of the above that the present invention was developed. Among the objects and features of the invention is reducing the radiation exposure of staff in an x-ray laboratory.

A second object of the invention is substantially reducing primary radiation around an x-ray table and thereby permitting doctors to perform fluoroscopic based medical and surgical procedures with access to a patient without being exposed to excessive amounts of radiation.

A third object of the invention is reducing secondary radiation in the region around an x-ray table where doctors operate on a patient.

A fourth object of the invention is to minimize radiation leaking into a cubicle enclosing an x-ray table while the x-ray table moves relative to the cubicle.

In one aspect of the present invention, a radiation protection system around an x-ray table is provided with a radiation-shielding wall, a radiation-shielding screen, and a radiation-shielding flexible interface between the wall and the x-ray table. The wall separates an x-ray emitter from an operating region where doctors and other medical personnel are in close proximity to a patient on the x-ray table. The screen is attached to and covers the x-ray table in the operating region such that the screen is interposed between the patient and the medical personnel. The interface has joints attached to the wall and a radiation-resistant skirt joining the cubicle and the x-ray table. At least one access port may be formed in the screen, and at least one radiation-shielding cloak can cover the access port and surround medical instruments that are threaded through the port and inserted into the patient.

In a second aspect of the present invention, a radiation protection system around an x-ray table is provided with a radiation-shielding cubicle, a radiation-shielding screen, and a radiation-shielding flexible interface between the cubicle and the x-ray table. The cubicle surrounds the doctors in the operating region. As in the first embodiment, the screen is attached to the x-ray table and interposed between the patient and the doctors, and the interface has joints attached to the cubicle and a radiation-resistant skirt joining the cubicle and the x-ray table.

Further features and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION OF THE INVENTION

Figure 1:
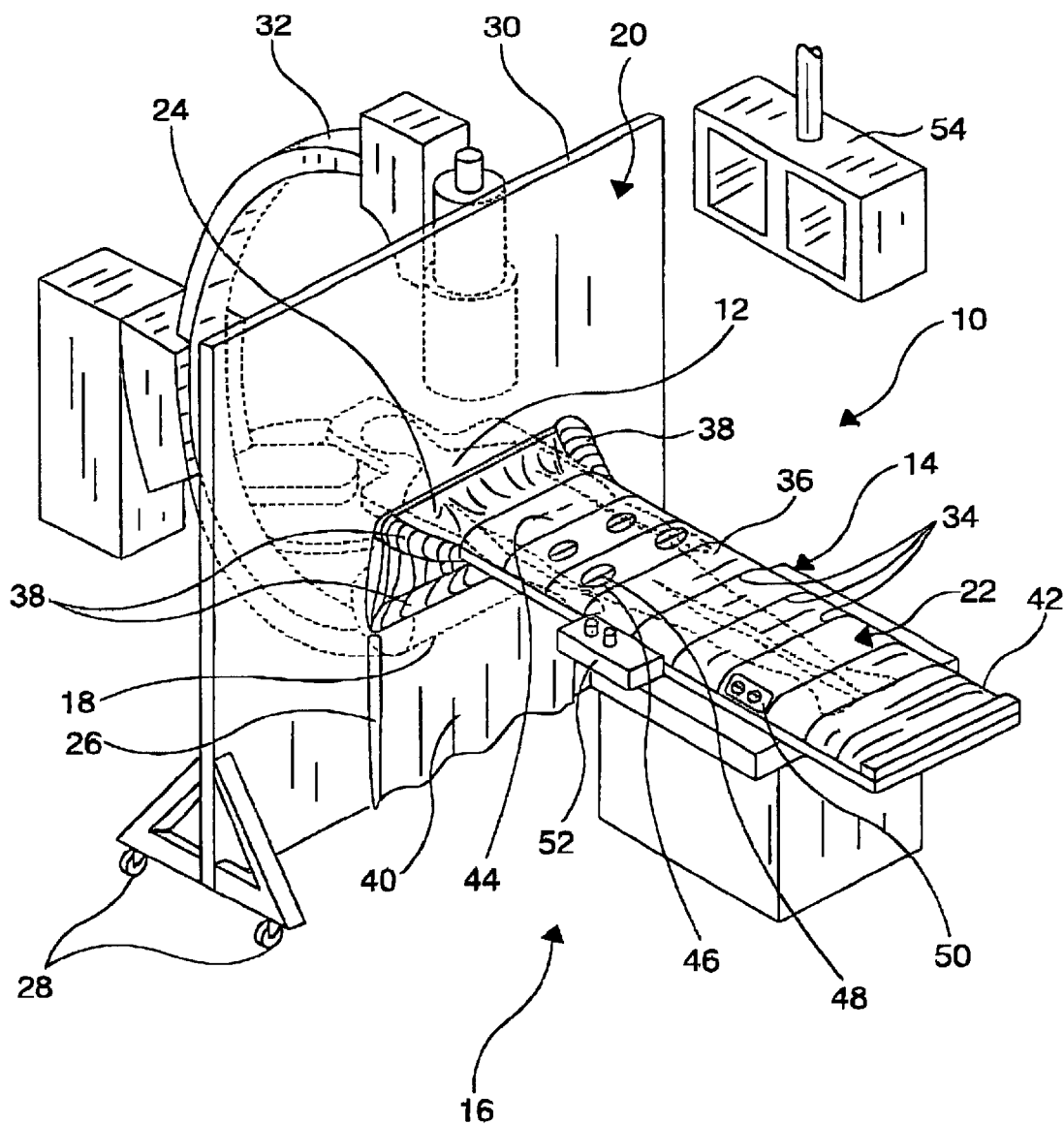
FIG. 1 illustrates a perspective view of a radiation protection system according to the present invention.

Referring to the accompanying drawings in which like reference numbers indicate like elements, FIG. 1 illustrates a radiation protection system 10 that covers a patient 12 on an x-ray table 14 and separates an operating region 16 from a C-arm x-ray emitter 18. The radiation protection system 10 includes a radiation-shielding wall 20, a radiation-shielding screen 22 on the x-ray table, and a radiation-shielding flexible interface 24 connecting the screen and x-ray table 14 with the wall 20. The wall 20 is constructed from well-known radiation-blocking materials and is preferably transparent, thereby permitting visual contact between doctors (not shown) in the operating region 16 and the patient 12. An opening 26 is provided in the wall 20 so that it can be moved over the x-ray table 14, and the wall 20 is preferably supported by retractable casters 28. Extending the casters 28 permits the wall 20 to be rolled into place, and retracting the casters sets the wall in place. The top of the wall 30 is preferably higher than the C-arm 32 at its highest extension.

The radiation-shielding screen 22 is movably attached to the x-ray table 14. The screen 22 has a plurality of screen supports 34 attached to the x-ray table 14 and a radiation-resistant partition 36 attached to the supports 34. When extended, the screen 22 covers the x-ray table 14 in the operating region 16 and the partition 36 is interposed between the patient 12 and the doctors. The flexible interface 24 has flexible joints 38 and a flexible, radiation-resistant skirt 40. The flexible joints 38 connect the wall 20 with the x-ray table 14 and hold the skirt 40. The skirt 40 joins the wall 20 to the screen 22 and covers the opening 26 in the wall. The flexible joints 38 and skirt 40 can extend, thereby allowing movement of the x-ray table 14 during the medical procedure without moving the wall 20.

Transferring the patient 12 to and from the x-ray table 14 is facilitated by detaching the flexible interface 24 from the wall 20 and moving the wall, and by retracting the screen 22 to the foot 42 of the x-ray table 14. During fluoroscopic procedures, it is preferable for the screen 22 to extend over the patient 12 from the foot 42 to the patient's mid abdomen region 44. The partition 36 may be formed from a flexible sheet of radiation-resistant material, permitting the screen 22 to fold like a curtain as the screen supports 34 slide along the table. It will be evident to those skilled in the art that other movable devices can be substituted for the sliding mechanism, including a screen that can rotate like an awning (not shown). Alternatively, the screen could be constructed from rigid panels or segments. Also, screen segments may be hingedly attached like an accordion or rollably attached like a roll-top desk or a pool cover, or conformably attached like a Venetian blind.

The screen 22 preferably includes at least one instrument port 46 through which doctors can operate on the patient with surgical equipment (not shown), including threading a catheter through the port 46 and inserting the catheter into the patient 12. For fluoroscopic procedures in which a catheter is inserted into the patient 12, it is preferable to have access to the patient through ports 46 over the patient's groin region near the femoral vessels. Each access port 46 can be covered by a radiation-shielding cloak 48 that is attached to the screen 22 around catheters. The cloaks 48 help protect the doctors operating around the x-ray table 14 from radiation scattering through their respective ports 46. The screen 22 may also have control ports 50, allowing connections to controls on the x-ray table (not shown), and the x-ray table 14 may also have a user interface 52 external to or coterminous with the screen 22. Access to the x-ray table's controls allows the doctors to adjust the position of the table throughout the procedure. It may also permit the doctors to control the position and orientation of the C-arm 32 and catheterization system monitors 54. As with other surgical equipment, the wall 20, screen 22, interface 24, and cloaks 48 can be sterilized. Alternatively or in combination removing the screen 22 from the x-ray table 14 and the interface 24 from the wall 20 to sterilize the equipment, the partition 36 and the skirt 40 may be covered by disposable, sterile pads (not shown).

With the radiation protection system 10 set in place, doctors and other medical personnel in the operating region 16 are shielded from the x-ray emitter 18 and x-ray scattering during radiologic procedures. The radiation-shielding wall 20 separates the operating region 16 from the x-ray emitter 18 to protect the doctors from exposure to most primary radiation from the x-ray emitter 18 and from secondary radiation that could be scattered from the C-arm 32. The radiation-shielding screen 22 is interposed between the doctors and the patient 12 to protect against most x-ray scattering from the patient 12 and the x-ray table 14. The radiation-shielding flexible interface 24 covers the opening 26 in the wall 20 and joins the wall with the x-ray table 14 and the screen 22 to protect-against most radiation leaking into the operating region 16 when the x-ray table is moved.

Figure 2:
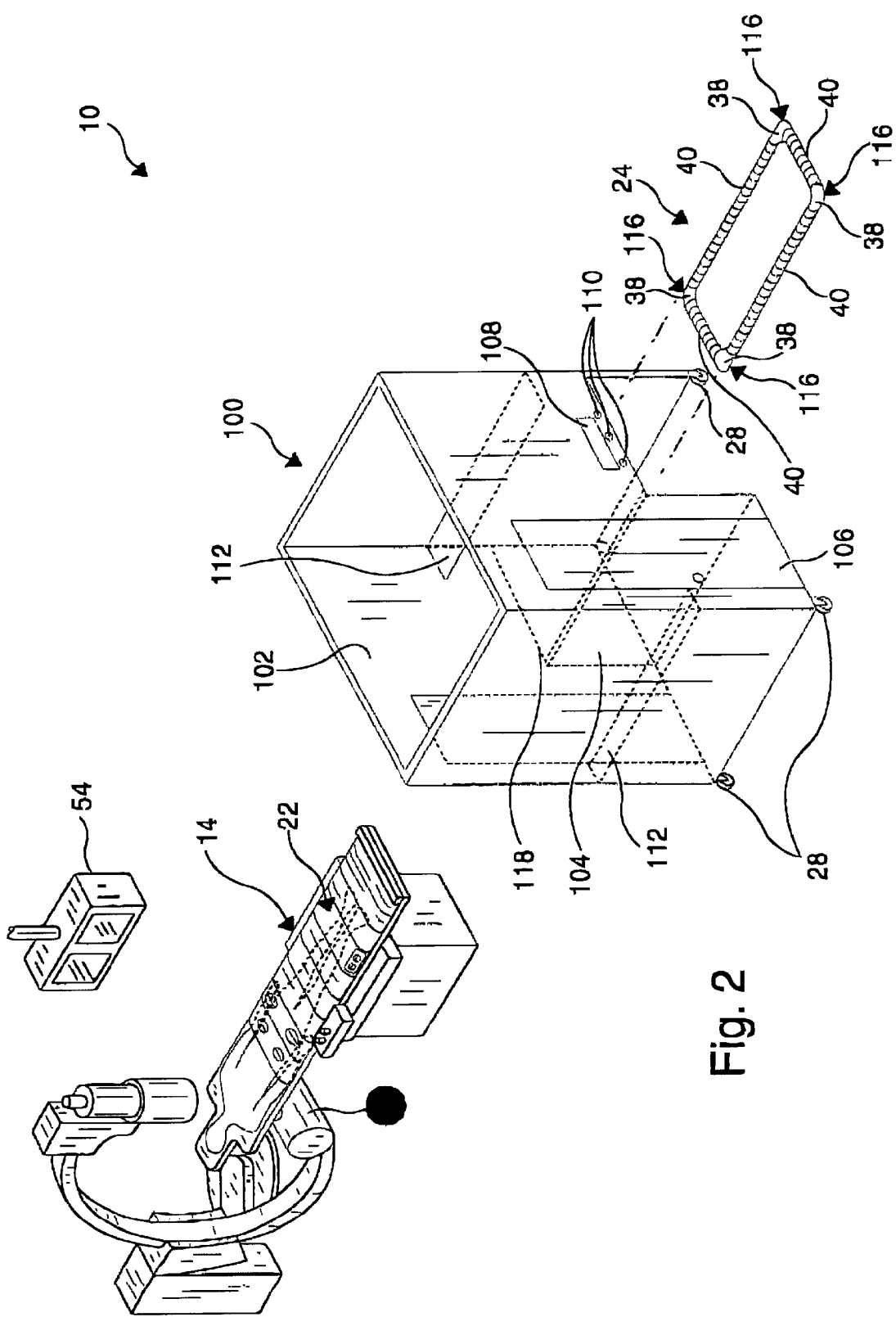
FIG. 2 illustrates a perspective view of an alternative embodiment of the radiation protection system in an un assembled state.
Figure 3:
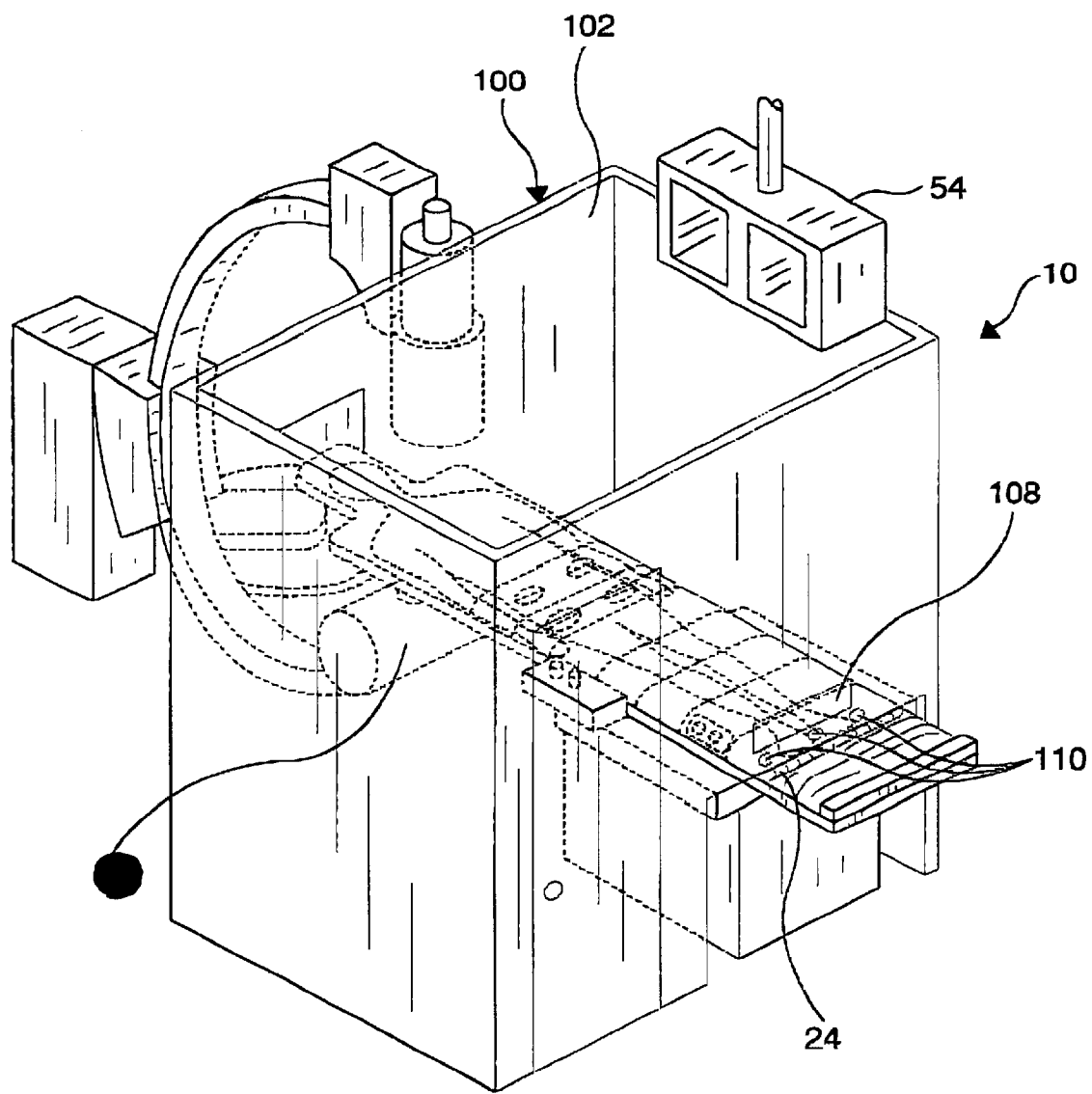
FIG. 3 illustrates a perspective view of the radiation protection system illustrated in FIG. 2 in an assembled state.
Figure 4:
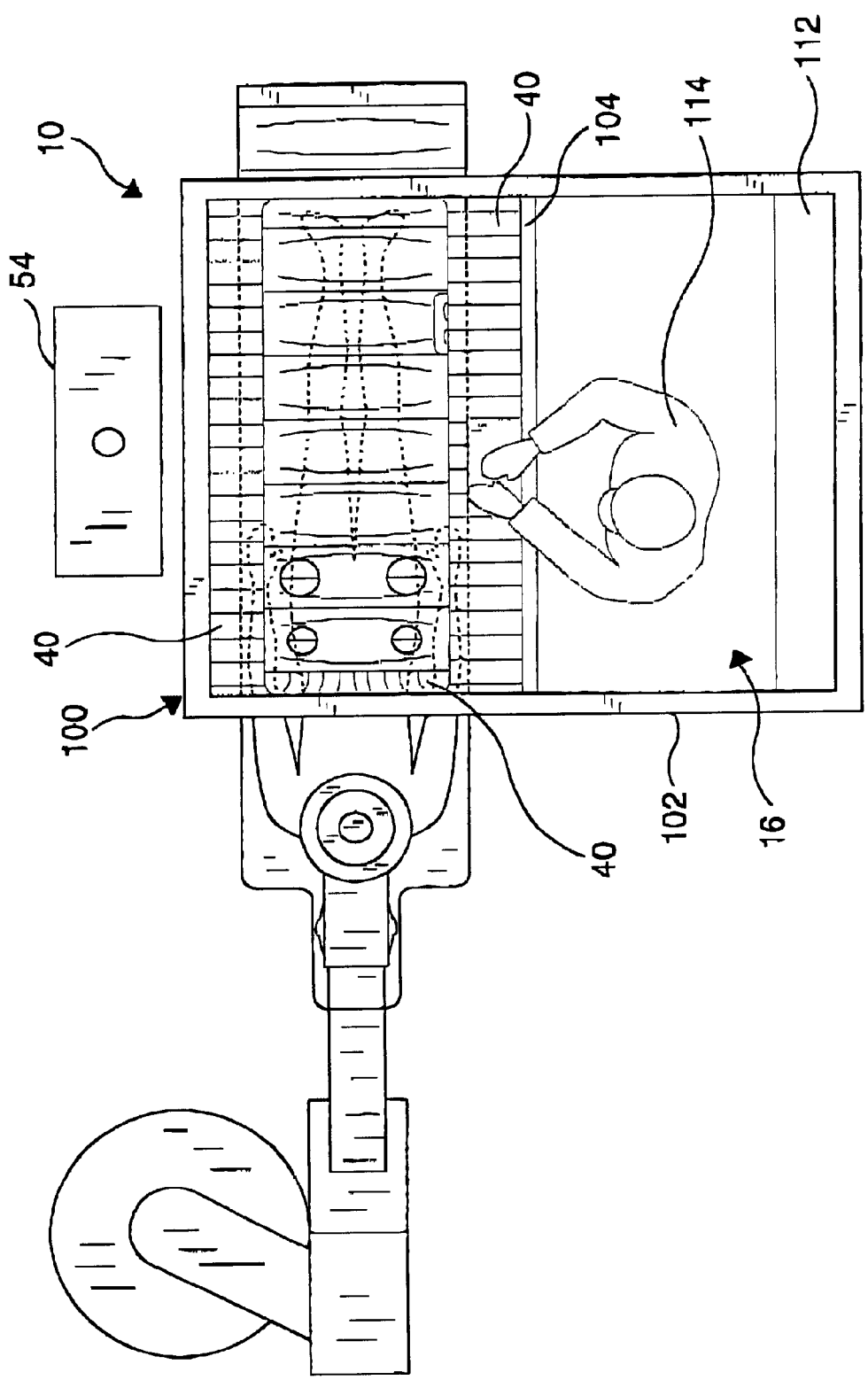
FIG. 4 illustrates a top plan view of the radiation protection system illustrated in FIG. 3.

FIG. 2 illustrates the un assembled sections of a second embodiment of a radiation protection system 10. As in the first embodiment, the radiation protection system 10 includes a radiation-shielding screen 22 and a radiation-shielding flexible interface 24. In the second embodiment, the radiation protection system 10 has a radiation-shielding cubicle 100, and the flexible interface 24 is mounted circumferentially around The x-ray table 14. As illustrated in FIGS. 3 and 4, the cubicle 100 encloses the operating region 16 when the system 10 is assembled. The entire cubicle 100 can be constructed from well known radiation-blocking materials and it can be constructed to allow for repeated disassembly and reassembly for portability and storage. A radiation-shielding cubicle wall 102 is interposed between the doctors and the C-arm x-ray emitter 18. The cubicle wall 102 is structurally and fuctionally similar to the radiation-shielding wall 20 in the first embodiment. Within the cubicle 100, the operating region 16 preferably provides adequate space for two doctors to operate on the patient 12. A half-wall 104 separates the operating region form the x-ray table 14, and the cubicle 100 extends over and around the x-ray table 14 adjacent to The operation region 16.

As with the wall 20 in the first embodiment, the cubicle 100 is preferably supported by casters 28 that can be retracted when the cubicle is in place over the x-ray table 14. The cubicle 100 also has at least one door 106. The cubicle 100 may contain access panels 108 for transferring equipment between the operating region 16 and the x-ray laboratory. The cubicle may also have tubing ports 110 for running catheters, tubes and other surgical equipment (not shown) from the patient 12 and the x-ray table 14 to other components in the x-ray laboratory. The cubicle may have its own ventilation system to maintain optimal ventilation and sterility, and may include shelves 112 for medical instruments. Shelves 112 in the back of the cubicle 100 can serve as a general staging table and shelves 112 suspended over the x-ray table 14 could serve as platform, allowing quick access to equipment by a doctor or other medical personnel 114. As in the first embodiment, the cubicle 100 may also have monitors 54 to display fluoroscopic and other physiologic images, and the cubicle 100 may include an audio system for optimal communication between the medical personnel 114 and the rest of the laboratory.

In the second embodiment, each corner 116 of the flexible interface 24 is attached to the cubicle 100 through the flexible joint 38. As in the first embodiment, the flexible radiation-resistant skirt 40 is held between the joints 38 to cover an opening 118 in the wall 102 and to join the wall 102 with the x-ray table 14 and the screen 22. In the second embodiment, the skirt 40 also circumferentially joins the x-ray table 14 to the cubicle 100. As in the first embodiment, the flexible joints 38 and skirt 40 permit the x-ray table 14 to be moved during the procedure. Extending and retracting the radiation screen 22 is performed in a manner that is similar to the first embodiment, and transferring the patient 12 to and from the x-ray table is also performed a similar manner. In the second embodiment, the flexible interface 24 must be detached around its circumference so that the cubicle 100 can be moved and the screen 22 can be retracted to the foot 42 of the x-ray table 14.

The first and second embodiments use the same method for shielding doctors and other medical personnel 114 from the x-ray emitter 18 and x-ray scattering when working in the operating region 16 adjacent to the patient 12 on the x-ray table 14. In particular, doctors are shielded from most x-ray radiation by isolating the operating region from the x-ray emitter with the radiation-shielding wall 20, 102 and the radiation-shielding flexible interface 24, covering the patient with a radiation-shielding screen 22 adjacent to the operating region, and joining the wall and the screen with the flexible interface. The wall 20, 102 and the flexible interface 24 isolate the operating region 16 from the x-ray emitter 18. The flexible interface 24 attaches the x-ray table 14 to the wall 20, 102 through flexible joints 38, 116 and joins the screen 22 to the wall 20, 102 through a flexible radiation-resistant skirt 40. The second embodiment further isolates the operating region 16 with the half-wall 104 adjacent to the x-ray table 14 and uses the skirt 40 to: circumferentially join the x-ray table 14 with the cubicle 100.

In view of the foregoing, it will be seen that the several advantages of the invention are achieved and attained. The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. For example, the wall 20 in the first embodiment can be curved or hinged to partially surround the operating region 16. As another example, the cubicle 100 can be wider to extend over the foot 42 of the x-ray table 14, thereby enlarging the operating region 16 within the cubicle 100. Thus, the breadth and scope of the present invention should not be limited by any of the above-described exemplary embodiments, but should be defined only in accordance with the following claims appended hereto and their equivalents.

What is claimed is:

1. A radiation protection system for shielding medical personnel from most radiation from an x-ray emitter and from x-ray scattering during radiologic procedures in which the medical personnel operate in close proximity to a patient on an x-ray table, comprising:
   a radiation-shielding wall separating the medical personnel from the x-ray emitter and having an opening around the x-ray table;
   a radiation-shielding screen attached to the x-ray table and interposed between the patient and the medical personnel; and
   a radiation-shielding flexible interface joining said wall with the x-ray table and said screen, said flexible interface having a flexible radiation-resistant skirt covering said opening in said wall.

2. A radiation protection system according to claim 1 wherein said screen has an instrument port through which the medical personnel can operate on the patient.

3. A radiation protection system according to claim 2 further comprising a radiation-shielding cloak attached to said screen around said instrument port.

4. A radiation protection system according to claim 1 wherein said screen has a control port through which the medical personnel can control the x-ray table.

5. A radiation protection system according to claim 1 wherein said screen is movably attached to the x-ray table such that said screen can be retracted and extended.

6. A radiation protection system according to claim 1 wherein said screen is comprised of a plurality of screen supports slidably attached to the x-ray table and a radiation-resistant partition attached to said screen supports.

7. A radiation protection system according to claim 1 wherein said interface is comprised of a plurality of flexible joints connecting said wall with the x-ray table and said skirt is attached to said joints and joins said wall with said screen.

8. A radiation protection system for shielding medical personnel from most radiation from an x-ray emitter and from x-ray scattering during radiologic procedures in which the medical personnel operate with surgical equipment in an operating region adjacent to a patient on an x-ray table, comprising:
   a radiation-shielding cubicle surrounding the medical personnel in the operating region and extending over the x-ray table adjacent to the operating region, said cubicle having a wall with an opening around the x-ray table;

a radiation-shielding screen attached to the x-ray table and interposed between the x-ray table and the medical personnel; and a radiation-shielding flexible interface circumferentially joining said cubicle with the x-ray table and said screen, said flexible interface having a flexible radiation-resistant skirt covering said opening in said wall.

9. A radiation protection system according to claim 8 wherein said screen has an instrument port through which the medical personnel operate on the patient with the surgical equipment.

10. A radiation protection system according to claim 9 further comprising a radiation-shielding cloak attached to said screen and surrounding the surgical equipment around said instrument port.

11. A radiation protection system according to claim 8 wherein said screen has a control port through which the medical personnel can control the x-ray table.

12. A radiation protection system according to claim 8 wherein said screen is movably attached to the x-ray table such that said screen can be retracted and extended.

13. A radiation protection system according to claim 8 wherein said screen is comprised of a plurality of screen supports slidably attached to the x-ray table and a radiation-resistant partition attached to said screen supports.

14. A radiation protection system according to claim 8 wherein said interface is comprised of a plurality of flexible joints connecting said cubicle with the x-ray table and said flexible radiation-resistant skirt is attached to said joints and joins said cubicle with said screen.

15. A radiation protection system according to claim 8 wherein said cubicle has a half-wall separating the operating region from the x-ray table.

16. A radiation protection system according to claim 8 wherein said cubicle has a shelf for placing surgical equipment.

17. A radiation protection system according to claim 8 wherein said cubicle has an access panel for passing surgical equipment.

18. A radiation protection system according to claim 8 wherein said cubicle has a tubing port for running surgical equipment.

19. A process for shielding medical personnel from an x-ray emitter and x-ray scattering in an operating region in close proximity to a patient on an x-ray table, the steps comprising:

isolating the operating region from the x-ray emitter with a radiation-shielding wall and a radiation-shielding flexible interface;

covering the patient with a radiation-shielding screen adjacent to the operating region; and joining said wall and said screen with said flexible interface.

* * * * *

UNITED STATES PATENT AND TRADEMARK OFFICE
CERTIFICATE OF CORRECTION

PATENT NO.    : 6,448,571 B1                                             Page 1 of 1
DATED         : September 10, 2002
INVENTOR(S)   : Goldstein, James A.

It is certified that error appears in the above-identified patent and that said Letters Patent is hereby corrected as shown below:

<u>Drawings,</u>
Figure 2, "●" should be -- 18 --;
Figure 3, "●" should be -- 18 --;

<u>Column 4,</u>
Line 40, the space between "un" and "assembled" should be removed;
Line 47, replace "The" with -- the --;
Line 62, replace "The" with -- the --; and <u>Column 5,</u>
Line 31,  -- in -- should be added between "performed" and "a"
Line 56, remove ":" that appears after "to."

Signed and Sealed this

First Day of April, 2003

JAMES E. ROGAN
*Director of the United States Patent and Trademark Office*